US008435461B2

(12) United States Patent
Kirby et al.

(10) Patent No.: US 8,435,461 B2
(45) Date of Patent: May 7, 2013

(54) ANALYTICAL DEVICES WITH INTEGRATED DESICCANT

(75) Inventors: Kevin J. Kirby, Valley Center, CA (US); Sarah Dennison, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 417 days.

(21) Appl. No.: 12/148,344

(22) Filed: Apr. 17, 2008

(65) Prior Publication Data

US 2008/0311002 A1    Dec. 18, 2008

Related U.S. Application Data

(60) Provisional application No. 60/925,592, filed on Apr. 20, 2007.

(51) Int. Cl.
*G01N 33/48* (2006.01)

(52) U.S. Cl.
USPC ............ 422/412; 422/401; 436/518; 436/169

(58) Field of Classification Search .......................... None
See application file for complete search history.

(56) References Cited

U.S. PATENT DOCUMENTS

| | | |
|---|---|---|
| 5,223,220 A | 6/1993 | Fan et al. |
| 5,415,994 A | 5/1995 | Imrich et al. |
| 5,763,262 A | 6/1998 | Wong et al. |
| 5,770,460 A | 6/1998 | Pawlak et al. |
| 5,900,379 A | 5/1999 | Noda et al. |
| 5,962,333 A * | 10/1999 | Incorvia et al. ................ 436/169 |
| 6,187,269 B1 | 2/2001 | Lancesseur et al. |
| 6,338,969 B1 * | 1/2002 | Shareef et al. ................ 436/518 |
| 6,558,528 B1 * | 5/2003 | Matzinger .................. 205/777.5 |
| 6,605,476 B2 | 8/2003 | Kobayashi |
| 6,613,405 B1 | 9/2003 | Hekal |
| 6,656,744 B2 | 12/2003 | Pronovost et al. |
| 6,730,494 B1 * | 5/2004 | Toranto et al. .................. 435/28 |
| 6,924,153 B1 | 8/2005 | Boehringer et al. |
| 7,005,459 B2 | 2/2006 | Hekal |
| 2005/0227371 A1 | 10/2005 | Gokhan |
| 2005/0272106 A1 * | 12/2005 | Moore et al. .................. 435/7.32 |
| 2006/0078986 A1 | 4/2006 | Ly et al. |

FOREIGN PATENT DOCUMENTS

| | | |
|---|---|---|
| EP | 1 046 913 A1 | 10/2000 |
| EP | 1 174 716 A1 | 1/2002 |
| EP | 1 754 971 A1 | 2/2007 |

(Continued)

OTHER PUBLICATIONS

International Search Report and Written Opinion for PCT//US2008/005100, search report dated Jul. 21, 2008, 13 pages (2008).

*Primary Examiner* — Sally Merkling
(74) *Attorney, Agent, or Firm* — Judy M. Mohr; Jacqueline F. Mahoney; McDermott Will & Emery LLP (57) ABSTRACT

An analytical device for performing an assay to determine the presence or approximate quantity of at least one analyte in a liquid sample is described. The device is manufactured to include an integrated desiccant within at least a test strip of the device. Addition of an integrated desiccant within the device improves signal to noise ratio, eases the manufacturing process, and saves in cost of production of the device.

7 Claims, 3 Drawing Sheets

FOREIGN PATENT DOCUMENTS

| | | | |
|---|---|---|---|
| GB | 2404022 A * | 1/2005 | |
| JP | 8-285842 A | 11/1996 | |
| WO | WO 99/47930 | 9/1999 | |
| WO | WO 02/50609 A1 | 6/2002 | |
| WO | WO2004/011942 A1 | 2/2004 | |
| WO | WO 2005/003732 A2 | 1/2005 | |
| WO | WO 2005/095967 A1 | 10/2005 | |
| WO | WO 2006/005483 A1 | 1/2006 | |
| WO | WO2007/105680 A1 | 9/2007 | |

* cited by examiner

Fig. 3

ANALYTICAL DEVICES WITH INTEGRATED DESICCANT

CROSS REFERENCE TO RELATED APPLICATIONS

The application claims the benefit of U.S. Provisional Application No. 60/925,592, filed Apr. 20, 2007, incorporated herein by reference in its entirety.

TECHNICAL FIELD

The subject matter described herein relates to devices for detecting the presence or approximate quantity of a chemical or biological substance (an analyte) in a biological sample. More particularly, the subject matter relates to immunoassay devices comprising a desiccant integrated into a portion of the device, and preferably into a portion capable of analyte detection.

BACKGROUND

Devices for the rapid qualitative and/or quantitative detection of analytes in a liquid sample often involve a sandwich type assay, frequently immunoassay, wherein certain reagents necessary for performance of the assay are located within the device. The device reagents are typically disposed within in the device in a dry form. During storage of the device prior to use, it is desirable to prevent adsorption and/or absorption of moisture onto the dry reagents, in particular for reagent that may be inactivated or desensitized by water molecules. Chemical drying agents, e.g., desiccants, for absorbing/adsorbing moisture are known in the art, and are typically included, for example, as a separate sachet in the package for the device or in a separate compartment of the device. There remains a need, however, to reduce or prevent moisture uptake by reagents and other components in a diagnostic assay device, where the desiccant is incorporated in such a way that it cannot contaminate the device reagents nor interfere with performance of the device. It is further desirable that such desiccant be incorporated in a manner that can improve manufacturing efficiencies, for example by decreasing manufacturing time and/or costs.

BRIEF SUMMARY

The following aspects of the present invention and embodiments thereof described and illustrated below are meant to be exemplary and illustrative, not limiting in scope.

In one aspect, analytical devices for performing an assay to determine the presence or approximate quantity of at least one analyte in a liquid sample are described. The devices have improved stability and/or manufacturability due to integration of a desiccant into one or more distinct regions within the device.

In another aspect, an analytical device for detecting the presence or approximate amount of an analyte in a sample is provided. The device comprises an analytical test strip and a desiccant material integrated into the analytical test strip.

In one embodiment, the desiccant is a material selected from molecular sieves and silica gels.

In certain other embodiments, the desiccant is integrated into the analytical test strip by laminating a desiccant-loaded sheet or film to the test strip or by securing a desiccant to the test strip by an adhesive.

In another embodiment, the desiccant is integrated into the test strip by a mechanical means.

The analytical device, in one embodiment, comprises an analytical device in the form of a dipstick.

Other objects, features and advantages of the compositions and methods of the present invention will be apparent from the following detailed description. It should be understood, however, that the detailed description and the specific examples provided herein, while indicating specific embodiments, are given by way of illustration only, since various changes and modifications within the spirit and scope of the invention will be apparent to those skilled in the art based upon the teachings in this detailed description.

DETAILED DESCRIPTION

I. Analytical Device

As used in this specification and the appended claims, the singular forms "a," "an" and "the" include plural referents unless the context clearly dictates otherwise.

In one aspect, an analytical device having a desiccant as an integrated component of the device is provided. In a preferred embodiment, the desiccant is an integral component of one or more regions of the test strip in the analytical device. The analytical device is preferably one for use in determining the presence or approximate quantity of one or more analytes in a fluid sample. As will be illustrated herein, a desiccant integrated into one or more regions of the analytical test strip region of the device improves manufacturability of the device. An integrated desiccant also reduces the likelihood that the assay reagents within the device will become contaminated, by moisture or by a non-integrated, loose desiccant, during storage, which contamination could impair the functionality of the device. An integrated desiccant can also be more cost efficient in product production.

A. Exemplary Assay Devices

Figure 1:
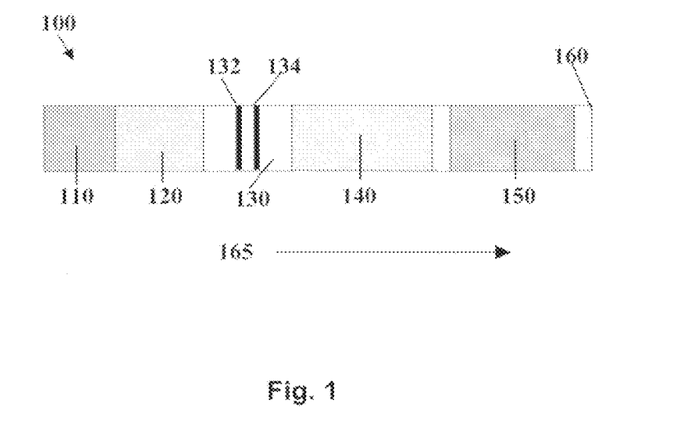
FIG. 1 is a view of an exemplary analytical device containing an integrated desiccant.

A variety of analytical diagnostic devices include a test region or test strip that contains reagents for detection of a sample analyte. Such devices have a variety of configurations and geometries, and a desiccant integrated into the test region of any of these analytical devices is contemplated. For purposes of illustrating a device having an integrated desiccant, an exemplary device is shown in FIG. 1. This device, and other devices, are described, for example, in U.S. Pat. Nos. 6,656,744; 6,924,153, and in U.S. Publication No. 2005/0227371, which are incorporated by reference herein. In brief, the device in FIG. 1 is known in the art as a 'dipstick' device and is capable of producing a relevant signal dependent upon the presence of a specific analyte in a liquid sample. Device 100 is comprised of a sample receiving pad or portion (which may optionally comprise a neutralization pad) 110, a label pad 120, a porous portion 130, comprising at least one test line 132, and, preferably, control line 134, an absorbent pad 140, and a desiccant portion 150, wherein the various portions of the device are secured, in fluid communication with one another, to a support member 160; provided however, that desiccant portion 150 may be adjacent but not in contact with (and thus not in fluid communication with) support 160. The support member 160 is typically fabricated from a non-porous rigid or semi-rigid material. Collectively, the support with the various portions secured thereto is referred to herein as a "test strip" or an "analytical test strip."

Sample receiving pad 110, label pad 120, and porous portion 130 can be directly touching or abutting the adjacent member thereto or can be in an overlapping arrangement with an adjacent member. For example, referring to FIG. 1, porous portion 130 and absorbent pad 140 may be assembled in overlapping relationship, provided however, they are arranged so as to not interfere with test line 132 or control line 134.

In FIG. 1, desiccant portion 150 is shown as a discrete, but integral, region at a distal end of the test strip. In a preferred embodiment, desiccant 150 is adjacent to and in contact with or nearly in contact with absorbent pad 140. Placing desiccant in this position is unrelated to functionality of either the test strip or desiccant but is selected for aesthetic reasons. It is contemplated, however, that a desiccant may be disposed at one or more of various locations along the test strip of the device. In a preferred embodiment, as shown in FIG. 1, the desiccant is an integral part of the test strip, but is not in direct contact with the absorbent pad. It is contemplated, however, that the desiccant can be included in the test strip so as to directly touch adjacent pads or portions, such as absorbent pad 140, or to overlap with one or more pads or portions of the test strip, without interfering with operation of the test strip. For example, and in one embodiment, desiccant portion 150 extends the length of the test strip of the device, disposed between support 160 and the various portions, where the extension of the desiccant can be continuous or non-continuous. When non-continuous, the desiccant portion is in contact with some, but not all portions of the test strip. In some embodiments, the desiccant portion may function as the support.

In a preferred embodiment, as shown in FIG. 1, sample receiving pad 110 is disposed at a proximal end of device 100, where a liquid sample is brought into contact with the device. Upon contact with sample receiving pad 100, the sample flows through the test strip of the device in the direction indicated by arrow 165, through the label pad 120 and porous portion 130 towards the distal end of the device. Test line 132 comprises an irreversibly immobilized reagent capable of interaction with analyte. The porous portion can optionally include a control zone 134 that comprises an irreversibly immobilized control reagent.

The opposing (or distal) end of device 100, comprises an absorbent pad 140 which serves as a sink zone.

In use, a fluid sample, such as a solution comprising a physiologic sample such as blood, serum, plasma, urine, saliva, mucous, spinal fluid, nasal wash, nasal aspirate, or the like, is introduced onto sample receiving pad 110 at the proximal end of the device. The sample may be added directly to the device in the original form as obtained from a subject, or may be treated, for example by addition of a buffering, extraction and/or other solution, prior to application to the device. Once added, the sample flows along a primary flow path, defined by the pads and portions, in the direction of arrow 165. In one embodiment, the sample receiving pad is formed from a non-bibulous material, such as the inert polyethylene material marketed as Porex™, or of a material with moderate bibulous nature such as spun nylon, which can be treated with an agent to confer non-bibulous characteristics if desired. The absorbent pad is preferably formed from materials that absorb and retain liquid and liquid components, including for example, latex, and which tends to restrict or prevent the reverse flow of components such as latex. By way of example, exemplary absorbent pad materials may consist of polyester, cellulose blends, nitrocellulose, and the like.

Porous portion 130 preferably is in fluid communication with label pad 120, as is the case in device 100. The porous material in porous portion 130 facilitates flow within the device by, for example, by absorbing fluid from the label pad 120 into or onto the porous portion. A "porous" material or component refers to a material comprising pores through which liquid may flow. By way of example, a porous material may be comprised of a network of insoluble material that supports liquid flow by capillary force. Typically, the pores within porous materials form randomly oriented, tangled open spaces connected to each other and forming a network of liquid-wicking ducts. Porous materials may be formed from natural and/or synthetic materials, fibrous or particulate. Porous materials suitable for use herein are well known to those of skill in the art and include, for example and without limitation, nitrocellulose-based materials, polymer-based materials, such as porous polyethylene, acrylic-based materials, such as spun laced acrylic, fibrous glass materials, paper materials and the like.

With continuing reference to use of device 100, when the sample contacts the label pad, the tag(s) located therein are mobilized. The tag(s) is (are) a component capable of binding an analyte present in the sample to form a complex. When sample contacts the label pad, the tag is released, for example by hydration or solubilization, becoming mobile with the sample. As sample and tag mix, they combine to form tagged analyte. Tags include, for example, antigens, haptens, antibodies, ligands, receptors, nucleic acid molecules, or chemical reactants. Tags may be linked to a directly detectable label, such as a colored latex particle, a light absorbing moiety, a chemiluminescent moiety or a particle, or the tag may be linked to an indirectly detectable label, such as an enzyme, for example including, without limitation, a hydrolase, esterase (for example, alkaline phosphatase) or oxidoreductase (for example, horseradish peroxidase).

In certain preferred embodiments, the label pad is comprised of a porous material, such as one of the materials described above. In alternative embodiments, one or more portions of the device, such as for example the sample receiving portion and/or label portion, are comprised of non-porous material. A "non-porous" material refers to a material through which insubstantial quantities of fluid (for example, liquid) flow. Typically, a water insoluble material is used as the non-porous material, and in preferred embodiments, the material is inert and impermeable to fluids used under normal assay conditions. Exemplary "non-porous" materials include, without limitation, thermoform or thermoplastic polymers (e.g. polystyrene, polyethylene, polycarbonate, polypropylene, fluoropolymer, or polyester, or a combination), glass, metals, ceramics or composite materials well known to those skilled in art. A non-porous surface can also be made of any material which is surface coated to render it impermeable to fluid. For example, a porous material can be coated with a low protein binding, non-water absorbing material such as a fluoropolymer resin, exemplified by Teflon™, or a polyester film, exemplified by Mylar™.

The sample, now comprising a tagged analyte if analyte is present therein, then flows into contact with the test line 132 where tagged analyte is captured. The test line typically comprises a binding reagent immobilized on or in a discrete region of the test strip, which binding reagent is capable of binding or otherwise interacting with and immobilizing the tagged analyte complex. Those of skill in the art will recognize that an analyte may be a component of the sample or a derivative or analogue of a sample component or the like. An irreversibly immobilized reagent refers to a reagent that is not appreciably solubilized or displaced by the passage of liquid sample under the liquid flow conditions applied in the routine or optimal operating conditions for the device. The binding reagent located in the test line is capable of binding or otherwise interacting with the analyte or a component of the analyte complex to retain (immobilize) the analyte or component. For example in a sandwich assay format, the mobilizable tag may contain an antibody that is a first binding partner of the target analyte and the test line may contain an immobilized antibody that is a second binding partner of the analyte (or analyte complex). Thus, at the test line, the analyte is "sandwiched" between the two antibodies. In a competitive assay system, the analyte displaces or competes with its analog or derivative in the test line, wherein the analyte or its derivative are labeled in the label pad upstream of the test line.

The sample continues to flow past the test line and, optionally, into contact with a control zone and then into the remaining porous material or other materials at the distal end of the device, such as absorbent pad 140, that, at least in part, act as a sink for the sample. The control zone is preferably located downstream of the test line, particularly where the device is designed for detection of a single analyte in a liquid sample. Where more than one analyte is to be detected and thus more than one test line is employed within the device, it may be preferable to locate a control zone between two test lines. The control zone may be designed to generate a signal that indicates that the liquid sample has indeed flowed through the device past the test line, and therefore, that the assay is working as designed. The control zone generally will comprise an immobilized reagent ("immobilized control reagent") that either is capable of generating a detectable signal as a result of interaction with a component of the sample or, more preferably, is capable of binding a control reagent comprising a detectable moiety. Optionally, the control zone may function as a "reference" zone to aid in determination of the presence or approximate quantity of the analyte in the aqueous sample or both control and reference zones may be employed in the device. The control zone may also function as a negative or positive control.

As described above, the test strip includes an integrated desiccant, exemplified in device 100 by desiccant portion 150. The desiccant portion of the device may be disposed in one or more regions of the device. By way of example, a desiccant region or layer can be adjacent, but not in direct contact with, an absorbent pad, as shown in FIG. 1. Alternatively, the desiccant can be directly adjacent and in physical contact with absorbent pad 140. Alternatively, the desiccant can be in an overlapping arrangement with a top or bottom surface of one or more pads, portions, or regions of the test strip, preferably without interfering with the test line(s) 132 or control line 134. In one embodiment, a desiccant portion is disposed as an intervening layer between support 160 and one or more of the pads, lines, or portions supported on the support. In another embodiment, support 160 comprises desiccant.

As can be appreciated, the desiccant is an integral part of the test strip, by virtue of its being in direct contact with one or more regions (for example the support) of the test strip. The desiccant, in a preferred embodiment, is integrated into the device in the form of a film or membrane, for example, a polyurethane film having desiccant dispersed therein. An example of a desiccant in the form of a film or tape is described in U.S. Pat. Nos. 7,005,459 and 6,613,405, which are incorporated by reference herein, where a desiccant is entrained in a polymer that is manufactured into a film or tape. In this form, the desiccant provides a stable, non-reactive, non-corrosive material that does not leave particulates capable of interfering with performance of the device, as can occur when a desiccant in loose form or in a sachet is disposed in the housing or packaging of the device. The integrated desiccant need not be sequestered from other parts of the device, such as by placement away from certain portions of the device, by use of a protective coating over the desiccant, or by packaging of the desiccant within other materials to form a sachet or film that is removed prior to use of the device. That is, the integrated desiccant material may be in contact with the sample, need not be removed prior to use, and does not interfere with performance of the device.

The device can optionally include one or more conditioning reagent zone(s) that comprise(s) sample treatment reagents to improve the performance of the assay, including, e.g., changing the pH, salt concentration or metal ion concentration, adding or removing inorganic or organic components or detergents, blocking non-specific interactions or removal/filtering of large and/or interfering components of the sample, such as for example, red blood cells from whole blood samples. Conditioning zone(s) may be included at or near the point of sample application and/or on/in either or both porous or non-porous material.

B. Desiccants

Desiccants suitable for integration into the test strip of an analytical device, like that described above, can be selected from a wide variety of materials, and in a preferred embodiment is a material capable of extracting and retaining moisture from an ambient environment having a humidity of at least up to about 5% humidity, more preferably of up to about 10-12% humidity. Desiccant materials capable of moisture absorption by a physical absorption process are preferred, however, materials that combine with water to form a hydrate or that react with water to form a new compound within which the water is combined may also be used.

Desiccants that absorb by physical absorption of moisture include molecular sieves, silica gels, clays (e.g., montmorillimite clay), certain synthetic polymers, and starches. In one embodiment, the molecular sieve pore sizes in the desiccant are between about 3-15 Angstroms.

Examples of desiccants include, but are not limited to, alumina, bauxite, anhydrous calcium sulfate, water-absorbing clays, silica gel, zeolite and any of the other moisture-absorbing materials known to the art. Other exemplary desiccants are described in detail in U.S. Pat. Nos. 5,911,937, 6,214,255, 7,005,459, 6,613,405, and 6,130,263, which are incorporated by reference herein.

It will be appreciated that various moisture sensitive indicators, e.g. cobalt chloride, which change color to indicate extent of moisture uptake by the desiccant, can be optionally included, and some commercial desiccants include such an indicator compounded with the desiccant.

The stability, or useful lifetime, of the reagents within an analytical device is a function, at least in part, of the extent of exposure to humidity during storage or prior to use. The present device, having an integrated desiccant, provides a shelf-life adequate for commercial purposes and with expected improved shelf life as compared to currently available devices. Shelf-life can be evidenced by, for example, the test reagents, such as an antibody, remaining capable of interaction with an analyte, for the duration of the shelf-life period.

C. Analytical Device with Integrated Desiccant

A desiccant can be integrated into the test strip of an analytical diagnostic device in a variety of configurations and by a variety of attachment techniques. In a preferred embodiment, the desiccant in integrated into the test strip in the form of a film. For example, a desiccant incorporated into an elastomeric polymer can be coated onto a support or a release paper to form a flexible desiccant-loaded polymer film. The film can be coated directly onto one or more regions of the test strip, or can be secured to one or more regions of the test strip by an attachment technique.

In one embodiment, a desiccant is secured to one or more regions of a test strip using an adhesive. Examples of adhesives include, but are not limited to paste, putty, rubber cement, mucilage, birdlime, sealant, epoxy, and stickum. In other embodiments, the desiccant is integrated into the device by lamination of a desiccant or desiccant-containing material to one or more regions of a test strip. In another embodiment, the desiccant is integrated into the device by a mechanical means. Examples of a mechanical means include, but are not limited to stapled, riveted, tethered, pinned, strapped, leashed, cinched, wrapped, laced, hemmed, fused, bound, tied, fastened, soldered, merged, welded, and sealed.

In a preferred embodiment, the diagnostic assay device described herein is primarily employed in assaying either antigens or antibodies through the formation of an immune complex. However, it will be appreciated that the device need not be limited to an assay of these molecules. The device merely requires a first molecule that recognizes and binds a second molecule. The first molecule can be conveniently termed a ligand-recognition molecule, and the latter a ligand. While antibody and antigen are preferred aspects of a ligand-recognition molecule and ligand respectively the device can be used with a variety of ligands and ligand-recognition molecules. For example, hormone receptor molecules are a type of ligand recognition molecule and can be attached to the solid matrix material, and used to assay for the corresponding hormone ligand. Alternatively, a hormone could be bound to the matrix material and used to assay for hormone receptors. It will be apparent to those skilled in the art that there are many such combinations of ligand-recognition molecules and ligands suitably employable in the present immunodiagnostic device.

Devices containing an integrated desiccant were prepared as described in Examples 1 and 2, for detection of influenza A (with influenza B test line included thereon) and Strep A. Devices without an integrated desiccant were fabricated, to serve as a comparative control. The devices were stored at 45° C. and tested weekly to evaluate the device ability to detect influenza or Strep, applied to the device in a standard test solution. Results for the devices for diagnosis of influenza are shown in FIGS. 2A-2B and for diagnosis of Strep A in FIG. 3.

Figure 2A:
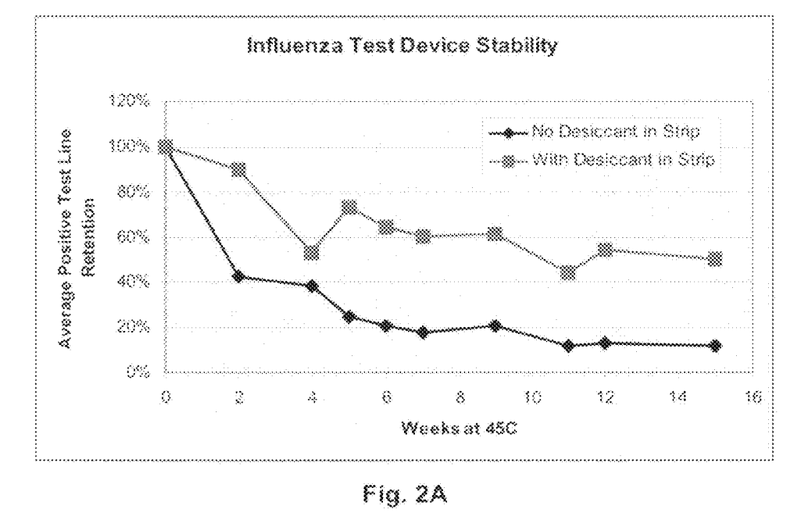
FIGS. 2A-2B are graphs showing the percentage of devices (fabricated either with (triangles) or without (squares) an integrated desiccant) at each time point that produced a positive test line (indicating presence of influenza A analyte), as a function of time, in weeks or days, respectively, of storage of the devices at 45° C.
Figure 2B:
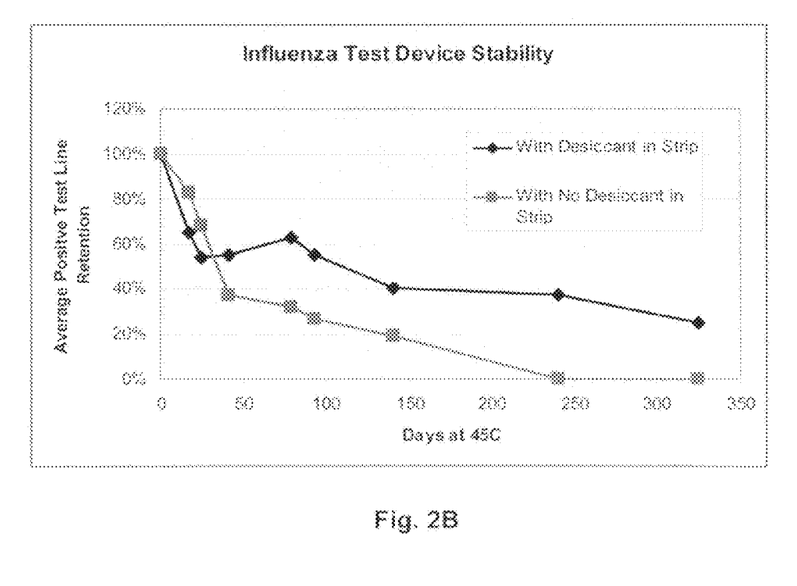

In FIGS. 2A-2B, the number of devices tested at each time point that had a positive test line relative to the total number of devices tested at each time point is shown. Devices with an integrated desiccant (triangles) consistently exhibited a positive test line, relative to the devices without an integrated desiccant (squares), for detection of influenza A and B.

Figure 3:
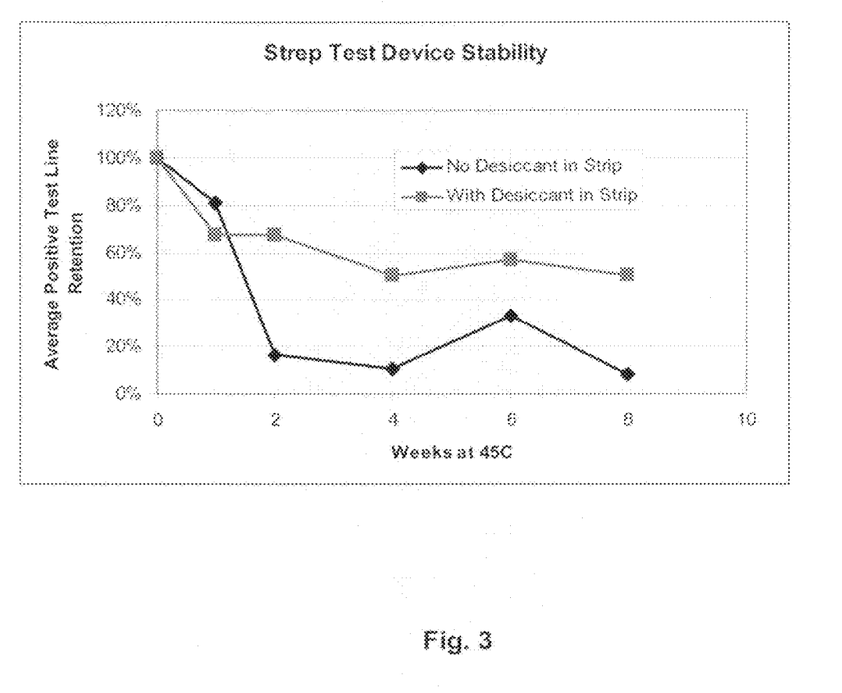
FIG. 3 is a graph showing the percentage of devices (fabricated with (triangles) an without (squares) an integrated desiccant) at each time point that produced a positive test line (for detection of Strep A), as a function of time, in weeks, of storage of the devices at 45° C.

Devices for detection of *Streptococcus pyogenes* ("Strep A") were prepared as described in Example 2, and the test results after storage at 45° C. are shown in FIG. 3. The number of devices tested at each time point that had a positive test line upon application of a test solution containing Strep A relative to the total number of devices tested at each time point is shown. Devices with an integrated desiccant (triangles) consistently exhibited a positive test line, relative to the devices without an integrated desiccant (squares), for detection of Strep A.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

II. EXAMPLES

The following examples are illustrative in nature and are in no way intended to be limiting.

Example 1

Preparation of Analytical Devices Comprising an Integrated Desiccant for Detection of Influenza A dipstick test device for detection of influenza A and influenza B was prepared as follows. A nitrocellulose membrane (Millipore) was laminated to a Mylar-Polyvinylchloride (PVC) backing. Two test lines for detection of influenza A and influenza B, respectively, were applied to the nitrocellulose membrane by spotting with a solution of anti-influenza A/nucleoprotein (NP) and a solution of anti-influenza B/NP. A control line was applied to the nitrocellulose membrane by spotting a solution of streptavidin-bovine serum albumin (BSA) conjugate. The layer was air dried for 5 minutes.

Solutions containing anti-influenza A nucleoprotein-coupled latex particles and anti-influenza B nucleoprotein-coupled latex particles and biotinylated BSA control beads were dispensed on an acrylic fiber to form a label pad. The pad was allowed to dry for 5 minutes.

The label pad and a sample receiving pad were laminated by hand to the Mylar-PVC, in a standard lateral flow test configuration (see, for example, FIG. 1). A cellulose absorbent pad was laminated adjacent to the nitrocellulose membranes containing the test and control lines.

A desiccant film was then laminated onto the Mylar-PVC adjacent to the absorbent pad in some of the devices. For comparison, devices without the desiccant film were prepared.

Immediately after device construction and then weekly after storage at 45° C., a device was tested to evaluate its ability to detect influenza A analyte in a standard test solution. The test sample containing recombinant influenza A/NP was applied to the receiving pad and the test lines were observed to determine if the device was able to detect influenza A/NP. Results from duplicate experiments are shown in FIGS. 2A-2B with FIG. 2A showing data taken at various weekly time points over 16 weeks and FIG. 2B showing data taken at various daily time points over about 350 days.

Example 2

Preparation of Analytical Devices Comprising an Integrated Desiccant for Detection of *Streptococcus pyogenes*

A dipstick test device for detection of *Streptococcus pyogenes* ("Strep A") was prepared as described in Example 1, except a single test line was formed by spotting a solution of rabbit Anti-Strep A antibody, and a control line was formed by spotting a solution anti glucose oxidase. Strep A coupled test latex beads and Glucose Oxidase control latex beads were applied to the acrylic fiber to form the label pad.

Devices identical in all respect except for the presence or absence of a desiccant film were tested immediately after device construction and then weekly after storage at 45° C. by applying a test sample containing Strep A. Results are shown in FIG. 3.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A lateral flow immunoassay device for detection of an analyte in a biological sample, comprising:
   an analytical test strip comprising
   a support member,
   a plurality of porous pads in fluid communication, said plurality of porous pads in contact with the support member and including, in sequence, a sample receiving pad, a label pad containing mobile tag reagents, a test pad containing immobilized binding reagents, and an absorbent pad which serves as a sink zone, and
   a desiccant portion, comprising a film or membrane having desiccant dispersed therein, which is laminated to the analytical test strip, such that said desiccant is disposed adjacent but not in contact with the absorbent pad,
   wherein said desiccant portion remains integral with the analytical test strip during use thereof.

2. The device of claim 1, wherein the desiccant portion comprises a material selected from the group consisting of molecular sieves and silica gel.

3. The device of claim 1, wherein the analytical test strip is in the form of a dipstick.

4. The device of claim 1, wherein said mobile tag reagents and immobilized reagents are capable of binding an influenza A analyte.

5. The device of claim 4, comprising two test lines within said test pad, containing immobilized reagents capable of binding influenza A and influenza B analytes, respectively.

6. The device of claim 1, wherein said mobile tag reagents and immobilized reagents are capable of binding a *Streptococcus pyogenes* analyte.

7. The device of claim 1, wherein the desiccant is integrated into the device by
   (i) providing a desiccant-loaded film or membrane; and
   (ii) laminating said desiccant-loaded film or membrane to the test strip.

* * * * *

UNITED STATES PATENT AND TRADEMARK OFFICE
CERTIFICATE OF CORRECTION

| | | Page 1 of 1 |
|---|---|---|
| PATENT NO. | : 8,435,461 B2 | |
| APPLICATION NO. | : 12/148344 | |
| DATED | : May 7, 2013 | |
| INVENTOR(S) | : Kirby et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this
Thirtieth Day of December, 2014

Michelle K. Lee
*Deputy Director of the United States Patent and Trademark Office*